US006693290B2

(12) United States Patent
Yamaguchi

(10) Patent No.: US 6,693,290 B2
(45) Date of Patent: Feb. 17, 2004

(54) ELECTRON BEAM PROCESSING DEVICE

(75) Inventor: Masanori Yamaguchi, Hyogo-ken (JP)

(73) Assignee: Ushio Denki Kabushiki Kaisha, Tokyo-to (JP)

( * ) Notice: Subject to any disclaimer, the term of this patent is extended or adjusted under 35 U.S.C. 154(b) by 169 days.

(21) Appl. No.: 09/852,726

(22) Filed: May 11, 2001

(65) Prior Publication Data

US 2001/0040222 A1 Nov. 15, 2001

(30) Foreign Application Priority Data

May 12, 2000 (JP) ....................................... 2000-140484
May 12, 2000 (JP) ....................................... 2000-140490

(51) Int. Cl.$^{7}$ ............................ A61N 5/00; G21G 5/00; H01J 17/26

(52) U.S. Cl. ................................ 250/492.2; 250/492.1; 250/492.3; 313/231.31

(58) Field of Search ........................... 250/492.1, 492.3, 250/435

(56) References Cited

U.S. PATENT DOCUMENTS 4,617,237 A * 10/1986 Gupta et al. ................ 428/446
5,659,223 A * 8/1997 Goodman .................... 315/39
6,140,657 A 10/2000 Wakalopulos et al.
6,295,861 B1 * 10/2001 Tom et al. ................. 73/24.06
2001/0015412 A1 * 8/2001 Komori et al. .......... 250/492.3
2001/0040222 A1 * 11/2001 Yamaguchi .............. 250/492.2
2002/0074519 A1 * 6/2002 Yamaguchi .............. 250/492.1
2003/0042832 A1 * 3/2003 Yamaguchi ............ 313/231.31

* cited by examiner

*Primary Examiner*—John R. Lee
*Assistant Examiner*—Bernard Souw
(74) *Attorney, Agent, or Firm*—Oblon, Spivak, McClelland, Maier & Neustadt, P.C.

(57) ABSTRACT

The present invention provides an electron beam processing device capable of preventing the adhesion of contaminants to an exposed irradiation part of an electron beam tube, particularly a window thereof, in a processing chamber, and also capable of controlling the rise in temperature of this irradiation unit, and in this electron beam processing device, the irradiation part of the electron beam tube (1) is disposed in the processing chamber (2) and irradiates an electron beam onto a substance (6) disposed in the processing chamber (2), the irradiation part is constituted by a lid part with an opening (31) for allowing the electron beam to pass therethrough and a window (4) which covers the opening (31) and has a transmission part (41) permeable to the electron beam, and a cooling block (7) is arranged in contact with a part of the irradiation part excluding the transmission part (41).

6 Claims, 10 Drawing Sheets

(a)

(b)

ELECTRON BEAM PROCESSING DEVICE

BACKGROUND OF THE INVENTION

1. Field of the Invention

The present invention relates to an electron beam processing device for irradiating electron beams onto a substance and thereby subjecting it to various treatments, and particularly, relates to an electron beam processing device for curing an interlayer insulating film of a semiconductor device, which is called as SOG (Spin On Glass) film on a wafer, and forming film on other substances, and the like.

2. Description of the Related Art

FIG. 10 shows an example of a conventional electron beam processing device.

The electron beam tube 1 is connected to a high voltage power source which is not shown as a drawing, and has a function to irradiate electron beams onto a substance 6 in the processing chamber 2. The electron beam tube 1 has a lid part 3 and window 4, and the lid part 3 is made, for example, from silicon and provided to cover an opening of the electron beam tube 1. The lid part 3 has an opening 31 for allowing the electron beam, which is radiated from the electron beam tube 1 toward the processing chamber 2, to pass therethrough.

The window 4 which is covering this opening 31, is made from a material permeable to an electron beam, and is formed in a plurality. This window 4 is made, for example, from silicon and is formed of a thin film of several $\mu$m. Then, an irradiation part of the electron beam tube is formed of the lid part 3 and the window 4.

The substance 6 is placed on a heating plate 5.

According to this type of electron beam processing device, the substance 6 is irradiated with the electron beam which is radiated from the electron beam tube 1, and is processed effectively in a short time. Further, the substance 6 is processed more effectively by heating the substance on the heating plate 5.

Nevertheless, a conventional electron beam processing device has a problem that contaminants adhere to the window 4 and a drawback that the temperature of the window 4 rises high.

Specifically, when electron beams are irradiated onto an organic film such as a resist or the like as the substance, volatile contaminants are generated from this organic film, and the contaminants adhere to the irradiation part of the electron beam tube 1, particularly to the window 4. And when such contaminants adhere to the window 4, there arises a problem that the window 4 is oxidized or carbonized, and thereby the mechanical strength thereof is weakened, and, as a result, the window may become damaged.

Further, when such contaminants adhere to the window 4, there arises a problem that the energy of the electron beam passing through the window 4 is absorbed by such contaminants, and, as a result, the temperature of the window 4 rises high, and thereby the window may become damaged.

In addition, although not shown as a drawing, there are cases when process gas such as chlorine (Cl), fluorine (F) or the like is supplied during the processing, the silicon of the window 4 may be etched by these gases. Thus, there arises a problem that the mechanical strength of the window 4 is weakened, and thereby the window may become damaged.

Further, the heat for heating the substance 6 also transfers to the window 4 and thereby the temperature of the window 4 rises high. And, since the window 4 is formed of a thin film so as to effectively radiate electron beams, there arises a problem that the window 4 may be damaged in a few hours if the temperature of the window exceeds, for example, 400° C.

Moreover, when the lid part 3 is heated together with the window 4, gases are released from the various members arranged within the electron beam tube 1. These members, for example, are metal materials which are provided for generating electron beams and glass bodies structuring the outer periphery of the electron beam tube 1. And, when the gases are released, the gas pressure in the electron beam tube 1 rises high, and thereby electric discharge may be generated between the respective members in the electron beam tube 1, and, as a result, there arises a problem that a desired output of an electron beam can not be obtained.

SUMMARY OF THE INVENTION

An object of the present invention is to provide, in consideration of the various problems described above, an electron beam processing device capable of preventing contaminants from adhering to the irradiation part, particularly the window, which is exposed in the processing chamber of the electron beam tube, as well as controlling the rise of the temperature of this irradiation part.

In order to solve the aforementioned problems, the present inventor has adopted the following means.

The first means is a processing device characterized in that an irradiation part of an electron beam tube is disposed in a processing chamber and irradiates an electron beam onto a substance placed in the processing chamber, wherein the irradiation part is composed of a lid part with an opening for allowing the electron beam to pass therethrough and a window which covers the opening and has a transmission part permeable to the electron beam, and further, a cooling block is arranged in contact with a part of the irradiation part excluding the transmission part.

The second means is characterized in that means for spraying a cooling gas toward the window is provided in addition to the first means.

The third means is a processing device characterized in that an irradiation part of an electron beam tube is disposed in a processing chamber and irradiates an electron beam onto a substance placed in the processing chamber, wherein an inert gas spraying part for spraying inert gas toward the irradiation part and an outlet for such inert gas are provided near the irradiation part.

The fourth means is a processing device characterized in that an irradiation part of an electron beam tube is disposed in a processing chamber and irradiates an electron beam onto a substance placed in the processing chamber, wherein the processing chamber is composed of a first processing chamber which stores the irradiation part of the electron beam tube and has an inlet for inert gas, a second processing chamber which stores the substance placed and has an outlet for such inert gas, and the first processing chamber and second processing chamber are separated by a partition which has opening for the electron beam and inert gas.

The fifth means is characterized in that a gas inlet for flowing process gas necessary for processing the substance is provided at the lower side in the processing chamber, said process gas is introduced after the inert gas passed near the irradiation part of the electron beam tube.

REFERENCE NUMERALS IN THE FIGURES

Figure 1:
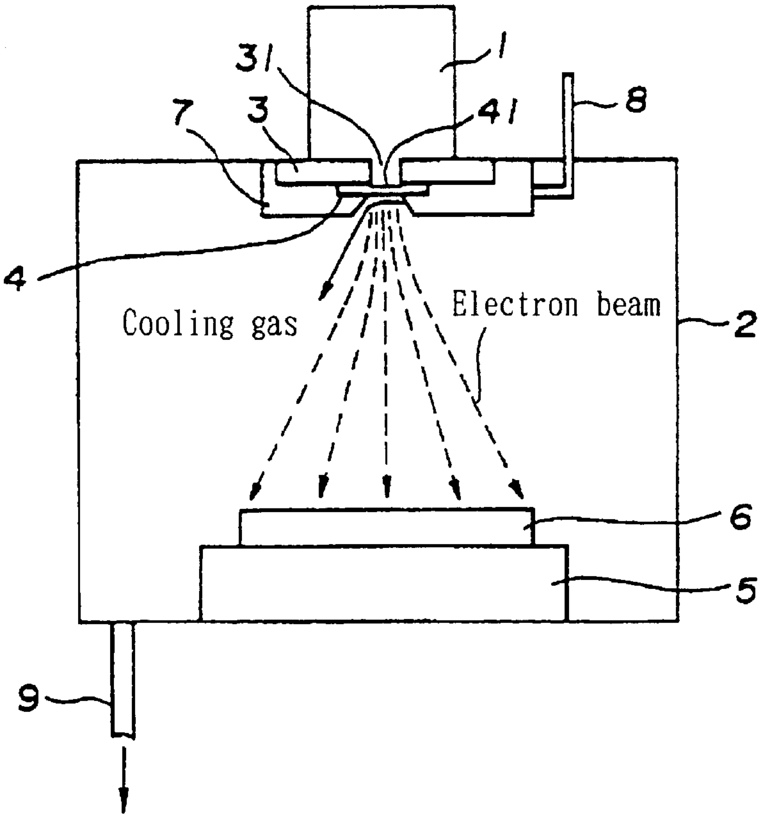
FIG. 1 is a front cross-sectional view showing the structure of the electron beam processing device according to the first embodiment of the present invention.

1 Electron beam tube
2 Processing chamber
21 First processing chamber
22 Second processing chamber
3 Lid part
31 Opening
4 Window
41 Election beam transmission part
42 Electron beam untransmission part
5 Processing plate
6 Substance to be processed
7, 10 Cooling block
71, 101 Cooling tube
721 Small pores
8, 11 Gas inflow tube
9 Gas exhaust tube
12 Partition
121 Partition opening
13, 14 Process gas inflow tube
15 Process gas supplying block
151 Process gas discharge pore

DESCRIPTION OF THE PREFERRED EMBODIMENTS

Foremost, the first embodiment of the electron beam processing device according to the present invention is described with reference to FIGS. 1 through 3.

Figure 2:
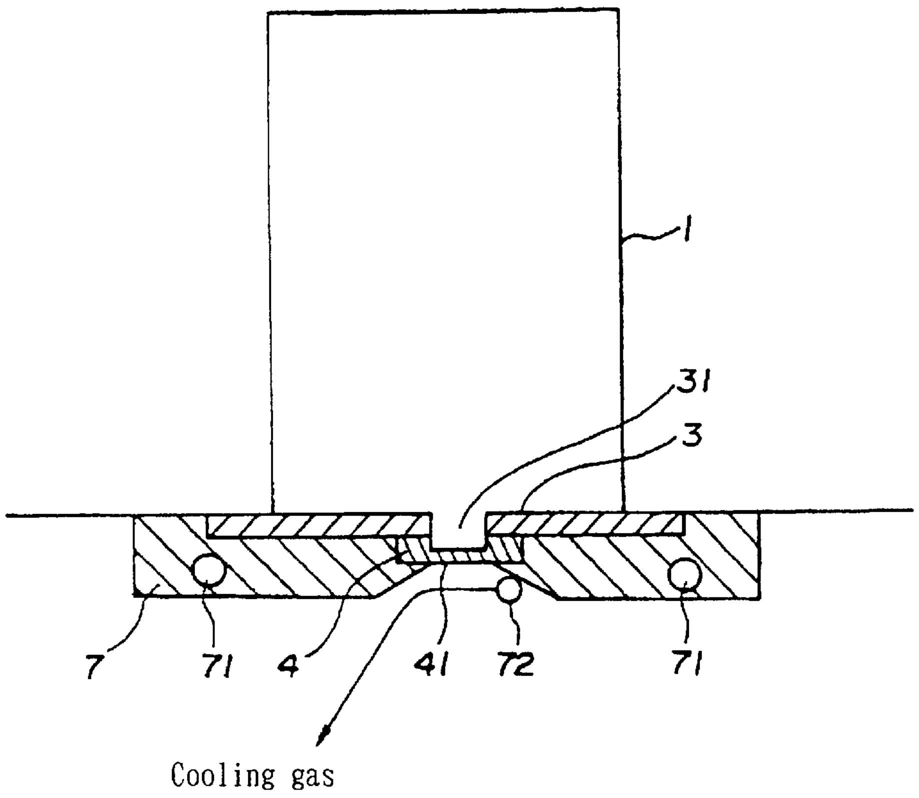
FIG. 2 is an enlarged view of the vicinity of the irradiation part of the electron beam tube 1 shown in FIG. 1.
Figure 3:
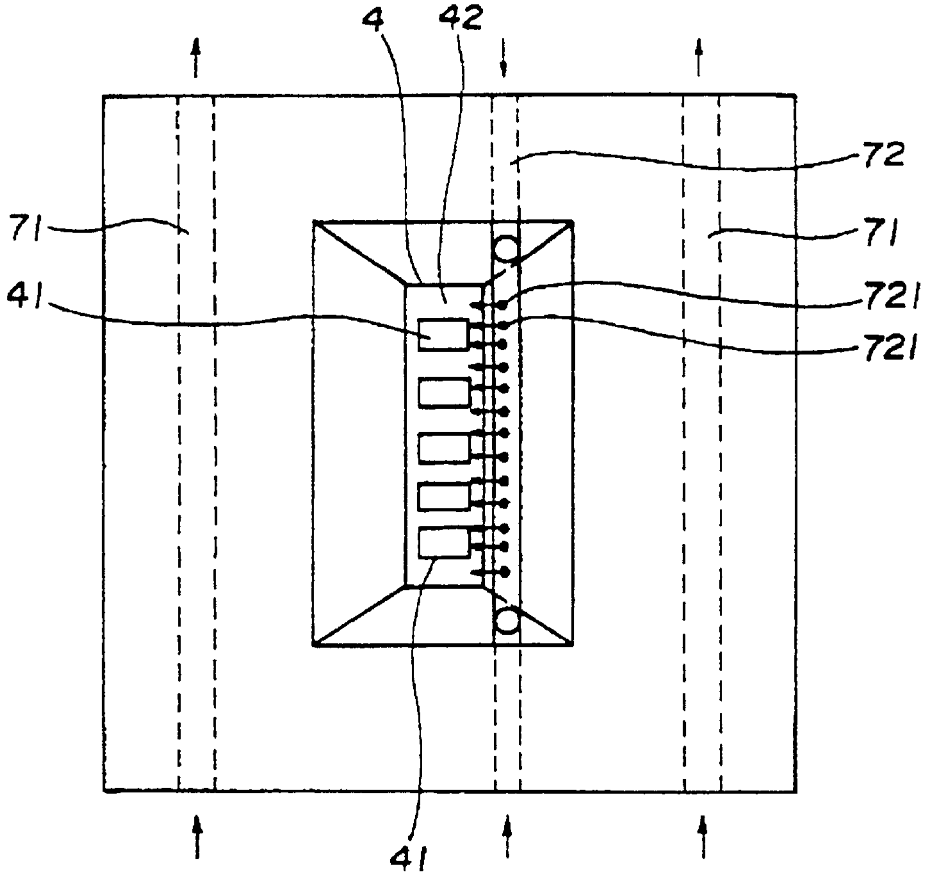
FIG. 3 is a bottom view showing the structure of the electron beam processing device according to the first embodiment of the present invention.

FIG. 1 shows a front cross-sectional view showing the structure of the electron beam processing device of this invention, FIG. 2 shows an enlarged view of the irradiation part of the electron beam tube, and FIG. 3 shows the bottom view of the electron beam tube.

In these drawings, an electron beam transmission part 41 and untransmission part 42 are formed on the window 4. The electron beam transmission part 41 is formed of thin, and a plurality of them are provided in order to transmit the electron beam thereto.

Then, in the irradiation part formed by the lid part 3 and window 4 as described above, a cooling block 7 is arranged in contact with the irradiation part so as to cover the part excluding the electron beam transmission part 41. This cooling block 7 comprises a cooling tube 71 for internally flowing a cooling fluid such as water or the like, and a cooling tube 72 for introducing cooling gas such as inert gas or the like from the outside of the cooling block 7 and spraying such cooling gas in the vicinity of the window 4.

A plurality of small pores 721 are provided on the cooling tube 72, and cooling gas is sprayed onto the window 4 through the pores. Cooling gas is introduced through the cooling gas inflow tube 8 and exhausted through the cooling gas exhaust tube 9.

Figure 10:
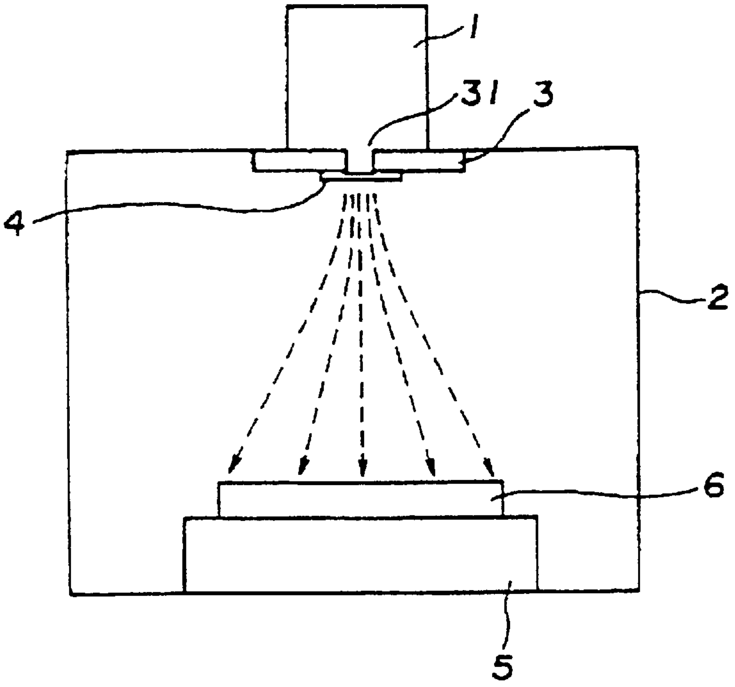
FIG. 10 is a front cross-sectional view showing the structure of a conventional electron beam processing device.

Further, components having the same reference numerals as those shown in FIG. 10 are of the same constitution, and the explanations thereof have been omitted.

In the electron beam irradiation device of this embodiment, the irradiation part formed by the lid part 3 and window 4 is cooled preferably by the cooling tube 71 provided on the cooling block 7, and thereby it is possible to prevent the rise of the temperature of the lid part 3 and window 4.

Moreover, in this embodiment, the cooling gas injected from the plurality of pores 721 in the vicinity of the window 4 is sprayed on the surface of the window 4. Thus, it is possible to effectively cool the window 4, and it is also possible to prevent contaminants generated in the processing chamber 2 from adhering to the window 4.

Further, a cooling tube 72 is provided on an end of the electron beam transmission part 41, and an additional cooling tube 72 can be provided on another end of the electron beam transmission part.

Another embodiment of the present invention is now described with reference to FIGS. 4 through 6.

Figure 4:
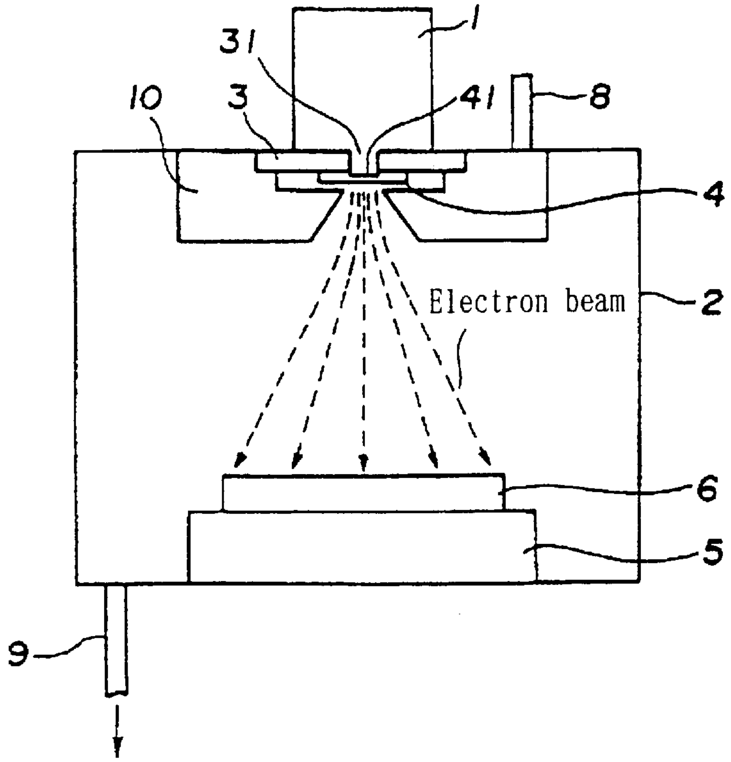
FIG. 4 is a front cross-sectional view showing the structure of the electron beam processing device according to the second embodiment of the present invention.
Figure 5:
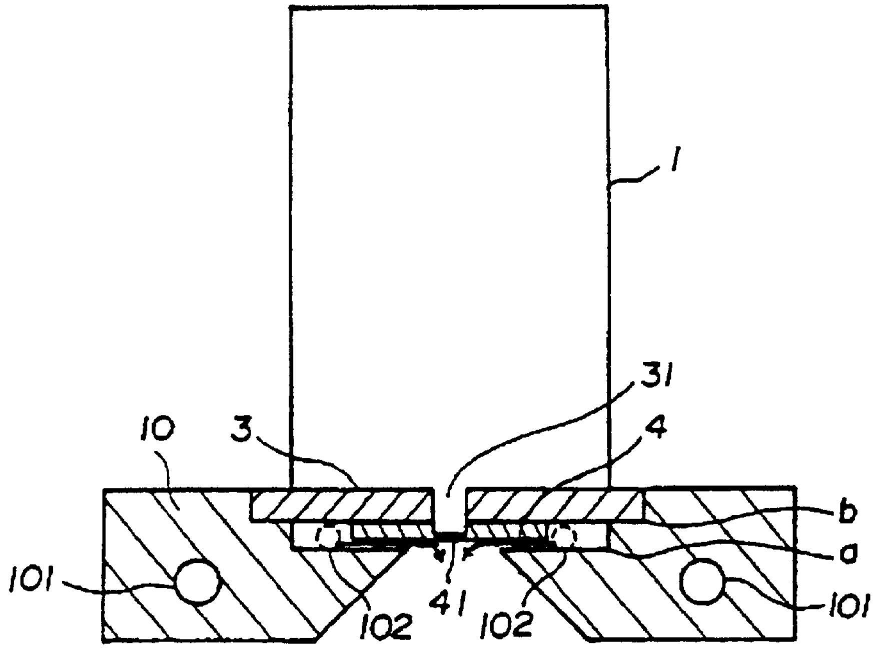
FIG. 5 is an enlarged view of the vicinity of the irradiation part of the electron beam tube 1 shown in FIG. 4.
Figure 6:
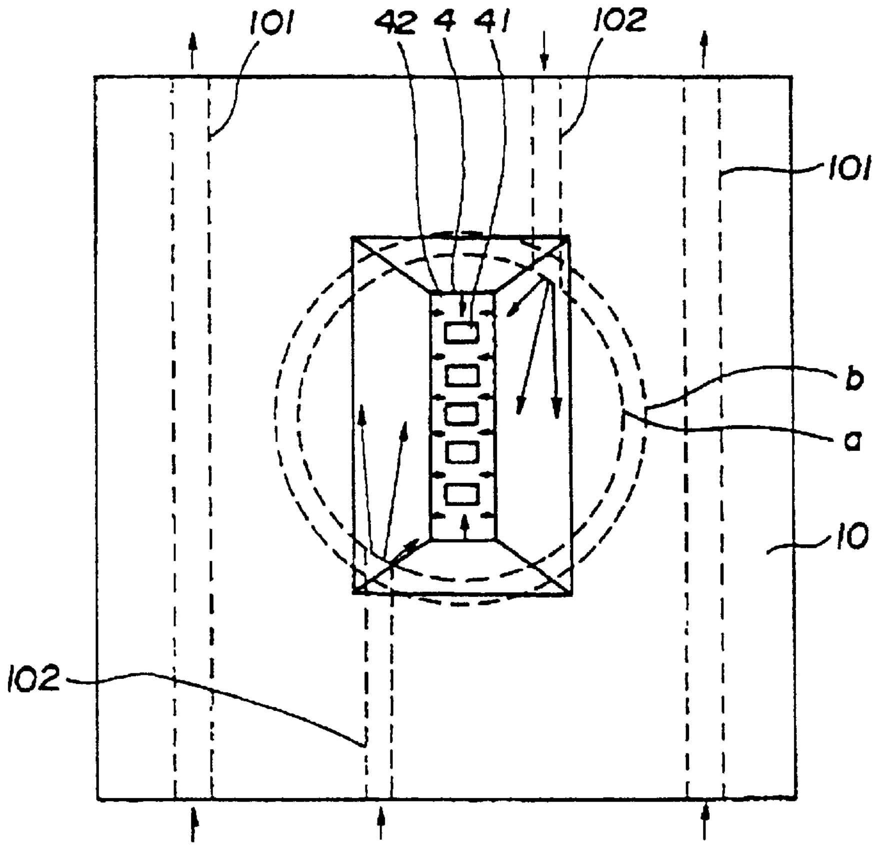
FIG. 6 is a bottom view showing the structure of the electron beam processing device according to the second embodiment of the present invention.

FIG. 4 is a front cross-sectional view showing the structure of the electron beam processing device according to the present invention, FIG. 5 is an enlarged view of the vicinity of the irradiation part of the electron beam tube 1 shown in FIG. 4, and FIG. 6 is a bottom view showing the structure of the electron beam processing device.

The present embodiment differs from the aforementioned embodiment on the structure regarding the cooling gas.

The cooling block 10 comprises a cooling tube 102 for externally introducing cooling gas such as inert gas or the like and spraying such cooling gas from the opening exposed between the cooling block 10 and the lid part 3.

Here, positions a and b shown in FIG. 5 are corresponding to the dotted-line positions a and b of the cooling block 10 shown in FIG. 6.

Further, components having the same reference numerals as those described above are of the same structure, and the explanations thereof have been omitted.

In the present embodiment, cooling gas is discharged from the opening of the cooling tube 102 into the space part formed between the cooling block 10 and lid part 3 and window 4, and thereby lid part 3 and window 4 can be cooled. It is thereby possible to prevent the rise of the temperature of the lid part 3 and window 4.

Moreover, in the above embodiment, it is not necessarily essential to provide the cooling tube 101 inside the cooling block 10, and it may be removed in certain cases. Here, in these cases, the block 10 does not function as a cooling block, but functions as a simple block. And, even in this sort of case, it is possible to preferably prevent the adhesion of contaminants to the window and to cool the irradiation part with the cooling gas.

Figure 7:
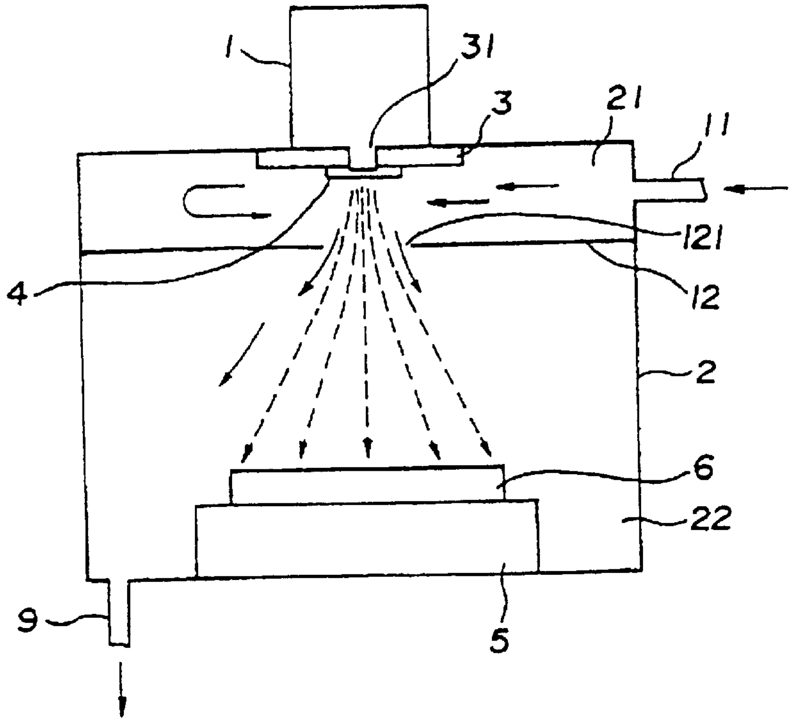
FIG. 7 is a front cross-sectional view showing the structure of the electron beam processing device according to the third embodiment of the present invention.

FIG. 7 shows another embodiment of the present invention and is a front cross-sectional view of the electron beam processing device of such embodiment.

In FIG. 7, the processing chamber 2 is constituted of a first processing chamber 21 and a second processing chamber 22. The first processing chamber 21 stores the irradiation part of the electron beam tube 1 and also has a gas inflow tube 11 for flowing the inert gas. And, the second processing chamber 22 stores a substance 6 mounted on the processing table 5 and has a gas exhaust tube 9 for exhausting gas containing the inert gas.

There is a partition 12 between the first processing chamber 21 and the second processing chamber 22 for differentiating the two. An opening 121 for allowing the electron beam and inert gas to pass therethrough is provided to the partition 12.

In FIG. 7 also, components having the same reference numerals as those described above are of the same structure, and the explanations thereof have been omitted.

In the electron beam irradiation device according to the present embodiment, the inert gas introduced from the gas inflow tube 11 to the first processing chamber 21 circulates around the irradiation part of the electron beam tube 1, more specifically near the window 4, and thereafter passes through the opening 121 and is exhausted from the gas exhaust tube 9 together with the contaminants generated during electron beam irradiation. This is as a result of that the inside of the processing chamber 2 is maintained in a state of desired pressure, preferably vacuum, for electrons to reach the substance to be processed.

Thus, it is possible to prevent the contaminants generated during the electron beam irradiation from adhering to the electron beam transmission part 41 of the window 4.

Figure 8:
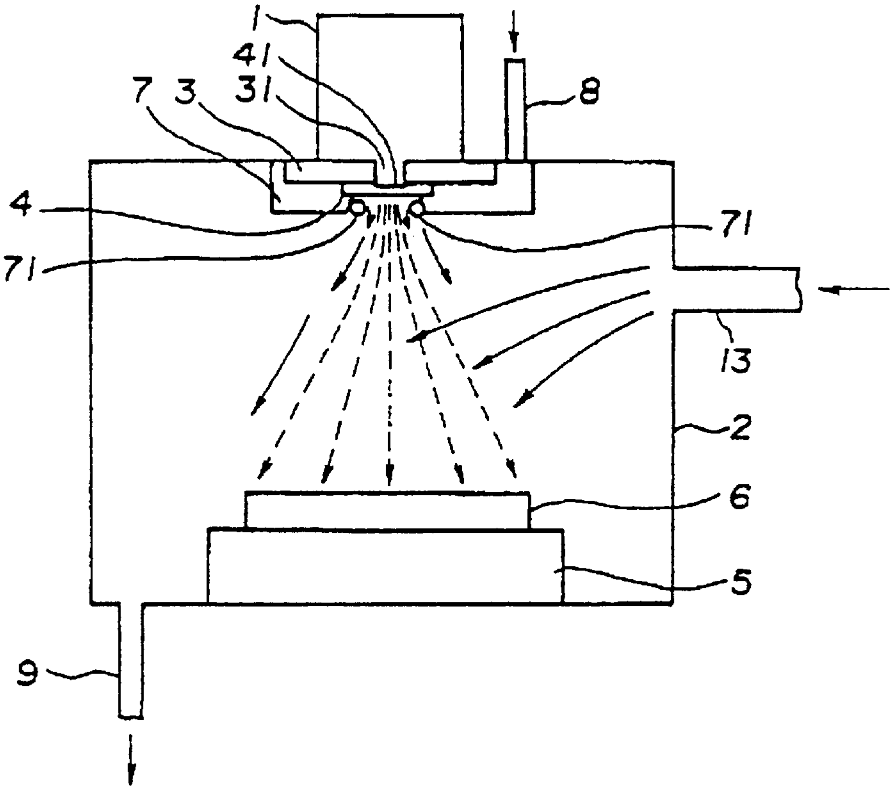
FIG. 8 is a front cross-sectional view showing the structure of the electron beam processing device according to the fourth embodiment of the present invention.

FIG. 8 shows another embodiment of the present invention and is a front cross-sectional view of the electron beam processing device of such embodiment.

In FIG. 8, the processing chamber 2 comprises a process gas inflow tube 13 for supplying process gas containing chlorine (Cl), fluorine (F) and the like during the electron beam processing of the substance 6.

In FIG. 8 also, components having the same reference numerals as those described above are of the same structure, and the explanations thereof have been omitted.

According to the present embodiment, an excess of the process gas among the process gas introduced from the process gas inflow tube 13 to the processing chamber 2 is exhausted from the gas exhaust tube 9 together with the contaminants generated during electron beam irradiation. This is as a result of that the inside of the processing chamber 2 is maintained in a state of desired pressure, preferably vacuum, for electrons to reach the substance to be processed similar to the aforementioned embodiment. And, pursuant to the flow of the inert gas, it is possible to prevent the process gas from flowing toward the irradiation part of the electron beam tube 1. Thus, it is possible to preferably prevent the problem that the window 4 is weakened or damaged as a result of the process gas making contact with the window 4 and thereby causing etching and so on.

Further, the structure having the process gas inflow tube shown in FIG. 8 may be employed in the structure of the processing device provided with the first processing chamber and second processing chamber shown in FIG. 7. In such a case, it goes without saying that the effects and advantages of the embodiments described above can be also achieved.

Figure 9:
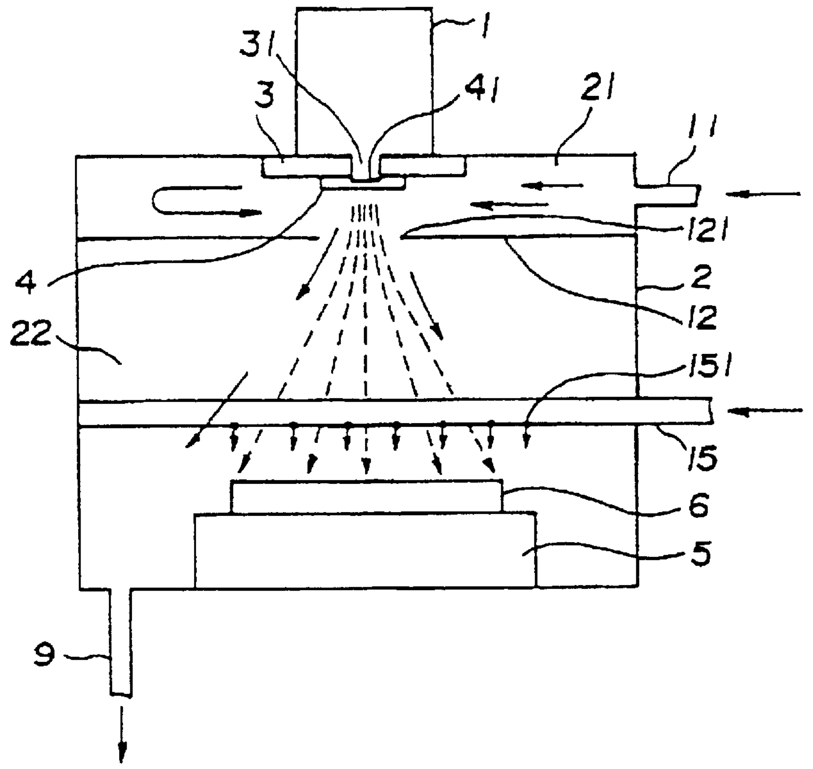
FIG. 9 is a front cross-sectional view showing the structure of the electron beam processing device according to the fifth embodiment of the present invention.
Figure 9:
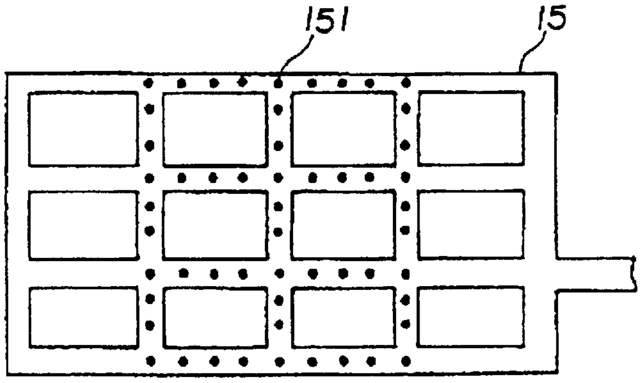

FIG. 9 shows another embodiment of the electron beam processing device according to the present invention.

FIG. 9(*a*) is a front cross-sectional view showing the structure of the electron beam processing device, and FIG. 9(*b*) is a plan view showing the structure of the process gas supply block shown in FIG. 9(*a*).

In FIG. 9, the second processing chamber 22 comprises a process gas supply block 15. Process gas containing chlorine (Cl), fluorine (F), or the like necessary for processing the substance 6 is supplied from the process gas supply block 15. And, the process gas supply block 15 comprises a process gas discharge pore 151 provided at a position for discharging process gas to the substance 6.

In FIG. 9 also, components having the same reference numerals as those described above are of the same structure, and the explanations thereof have been omitted.

According to the present embodiment also, the inert gas passes through the opening 121 and is exhausted from the gas exhaust tube 9 together with the contaminants generated during electron beam irradiation, and thereby prevents the contaminants generated during the electron beam irradiation from adhering to the window 4.

Moreover, the excess of the process gas among the process gas discharged toward the substance 6 from the process gas discharge pore 151 of the process gas supply block 15 is exhausted from the gas exhaust tube 9 together with the contaminants generated during electron beam irradiation. Thus, similar to the previous embodiments, it is possible to preferably prevent the process gas from weakening the mechanical strength of the window 4 and thereby causing damage thereto.

Furthermore, in the electron beam processing device in the aforementioned embodiments, although a structure that an electron beam tube is arranged at the upper part of the processing chamber and the substance is disposed at the lower part thereof is adopted, the structure of the electron beam processing device is not necessarily limited thereto. In other words, it is also possible to arrange the electron beam tube on one side face of the processing chamber and to dispose the substance on the other side face thereof.

As described above, according to the electron beam processing device of the present invention, since the cooling block is arranged in contact with the irradiation part, the irradiation part is cooled by the cooling block, and thereby it is possible to prevent the rise of temperature of the lid part and window of the irradiation part.

As a result, it is possible to control the release of gas from metal materials inside the electron beam tube and from the glass body structuring the outer periphery of the electron beam tube due to the rise of temperature of the irradiation part, and thereby to prevent the generation of abnormal electric discharge and the like within the electron beam tube.

Moreover, according to the electron beam processing device another aspect of of the present invention, since a cooling gas is sprayed onto the window, it is possible to effectively cool the window as well as to prevent contaminants and by-product materials generated in the processing chamber from adhering to the window. And, it is also possible to prevent a problem that the window is oxidized and carbonized due to the adherence of contaminants and by-product materials, and thereby mechanical strength thereof is weakened, and as a result, the window may be damaged.

Further, according to the electron beam processing device of another aspect of the present invention, since inert gas is sprayed onto the irradiation part of the electron beam tube from the gas spraying part, it is possible to prevent contaminants generated during electron beam irradiation from adhering to the irradiation part. And, it is also possible to prevent a problem that a part of the irradiation part is oxidized and carbonized due to the adherence of contaminants, and thereby mechanical strength thereof is weakened, and as a result, the irradiation part may be damaged.

Moreover, according to the electron beam processing device of another aspect of the present invention, it is possible to preferably exhaust contaminants generated during electron beam irradiation together with the inert gas flow. And it is thereby possible to prevent contaminants from adhering to the irradiation part of the electron beam tube.

Further, according to the electron beam processing device of another aspect of the present invention, since process gas is introduced at the lower side of the processing chamber, this process gas is exhausted together with contaminants generated during electron beam irradiation from the gas outlet. Thus, it is possible to prevent the process gas from causing damage to a part of the irradiation part by the effects of etching thereof and so on, and thereby weakening the mechanical strength of the irradiation part.

What is claimed is:

1. An electron beam processing device comprising:

an electron beam tube having an irradiation part permitting emergence of an electron beam from said tube into a processing chamber, the irradiation part being disposed in the processing chamber for irradiating the electron beam onto a substance placed in said processing chamber, said irradiation part being composed of a lid part with an opening for allowing the electron beam to pass therethrough and a window that covers said opening and has a transmission part permeable to the electron beam, and a cooling block internally flowing a cooling fluid and arranged in contact with a part of said irradiation part excluding the transmission part.

2. The electron beam processing device of claim 1, further comprising a member for spraying cooling gas toward said window is provided.

3. The electron beam processing device of claim 1, further comprising an inert gas spraying part for spraying inert gas toward said irradiation part provided in the vicinity of said irradiation part, and an outlet for the inert gas on the processing chamber.

4. The electron beam processing device of claim 1, wherein said processing chamber composes a first chamber that stores the irradiation part of said electron beam tube and has an inlet for inert gas, a second chamber that stores said substance and has an outlet for said inert gas, and a partition that separates the first chamber and the second chamber and has an opening for allowing said electron beam and said inert gas to pass therethrough.

5. The electron beam processing device of claim 3, further comprising a gas inlet for allowing process gas necessary for processing said substance to flow therein provided at the lower side in said processing chamber, said process gas is introduced after said inert gas passed near the irradiation part of said electron beam tube.

6. The electron beam processing device of claim 4, further comprising a gas inlet for allowing process gas necessary for processing said substance to flow therein is provided at the lower side of the first chamber, said process gas is introduced after said inert gas passed near the irradiation part of said electron beam tube.

* * * * *